(12) United States Patent
Fewell, Jr. et al.

(10) Patent No.: US 10,219,507 B1
(45) Date of Patent: Mar. 5, 2019

(54) NATURAL PESTICIDE STRUCTURES AND METHODS OF FABRICATION THEREOF

(71) Applicants: Richard L. Fewell, Jr., West Monroe, LA (US); Elbert Lawrence, West Monroe, LA (US)

(72) Inventors: Richard L. Fewell, Jr., West Monroe, LA (US); Elbert Lawrence, West Monroe, LA (US)

( * ) Notice: Subject to any disclaimer, the term of this patent is extended or adjusted under 35 U.S.C. 154(b) by 0 days.

(21) Appl. No.: 15/414,880

(22) Filed: Jan. 25, 2017

Related U.S. Application Data

(60) Provisional application No. 62/286,514, filed on Jan. 25, 2016.

(51) Int. Cl.
| | |
|---|---|
| *A01M 29/12* | (2011.01) |
| *A01N 65/22* | (2009.01) |
| *A01N 65/42* | (2009.01) |
| *A01N 65/44* | (2009.01) |
| *B65D 19/00* | (2006.01) |
| *A47B 37/04* | (2006.01) |
| *A47C 1/14* | (2006.01) |
| *A47C 1/02* | (2006.01) |
| *A47C 5/00* | (2006.01) |
| *A47B 96/00* | (2006.01) |
| *E04F 19/04* | (2006.01) |

(52) U.S. Cl.
CPC .......... *A01M 29/12* (2013.01); *A01N 65/22* (2013.01); *A01N 65/42* (2013.01); *A01N 65/44* (2013.01); *A47B 37/04* (2013.01); *A47B 96/00* (2013.01); *A47C 1/02* (2013.01); *A47C 1/14* (2013.01); *A47C 5/00* (2013.01); *B65D 19/0095* (2013.01); *E04F 19/04* (2013.01); *B65D 2519/00029* (2013.01); *B65D 2519/00064* (2013.01); *B65D 2519/00099* (2013.01); *B65D 2519/00273* (2013.01); *B65D 2519/00293* (2013.01); *B65D 2519/00323* (2013.01); *B65D 2519/00373* (2013.01); *B65D 2519/00825* (2013.01)

(58) Field of Classification Search
CPC ....... A01M 29/12; A01N 65/22; A01N 65/42; A01N 65/44; A01N 25/12; A01N 51/00; E04F 19/04; E04F 2019/0409
See application file for complete search history.

(56) References Cited

U.S. PATENT DOCUMENTS

| | | | | |
|---|---|---|---|---|
| 2,788,320 | A | * 4/1957 | Bracey | C09D 5/14 424/419 |
| 4,097,607 | A | * 6/1978 | Larson | A01N 35/02 252/365 |
| 4,876,090 | A | 10/1989 | Weisler | |

(Continued)

*Primary Examiner* — Beth A Stephan
(74) *Attorney, Agent, or Firm* — R. Keith Harrison (57) ABSTRACT

Methods of fabricating a natural pesticide structure include obtaining at least one raw material; forming at least one natural pesticide building material from the at least one raw material by applying at least one natural pesticide substance to the at least one raw material, the at least one natural pesticide substance having intrinsic pesticide properties and including any combination of the following: garlic, lavender, gardenia, peppermint, wintergreen and lemon grass; and fabricating a natural pesticide structure from the at least one natural pesticide building material. Natural pesticide structures are also disclosed.

19 Claims, 7 Drawing Sheets

(56) References Cited

U.S. PATENT DOCUMENTS

| | | | | |
|---|---|---|---|---|
| 4,965,070 A * | 10/1990 | Messina | | A01N 65/00 424/405 |
| 5,301,460 A | 4/1994 | Corbitt | | |
| 5,407,920 A * | 4/1995 | Dawson | | A01N 25/04 424/405 |
| 5,674,496 A * | 10/1997 | Etscorn | | A01N 65/38 210/633 |
| 5,783,258 A * | 7/1998 | Garapick | | B27K 3/0214 427/298 |
| 5,885,600 A * | 3/1999 | Blum | | A01N 65/00 424/405 |
| 6,231,865 B1 | 5/2001 | Hsu et al. | | |
| 6,231,937 B1 * | 5/2001 | Rader | | A01N 65/00 424/411 |
| 6,548,085 B1 | 4/2003 | Zobitne et al. | | |
| 6,821,631 B2 * | 11/2004 | Grantham | | B05D 7/08 106/15.05 |
| 6,923,977 B1 * | 8/2005 | Boyce | | A01N 65/00 424/405 |
| 7,575,765 B1 * | 8/2009 | Hughes | | A61K 36/00 424/725 |
| 7,806,155 B1 * | 10/2010 | Lee | | B27M 3/18 144/353 |
| 8,091,952 B2 * | 1/2012 | Risi | | B62D 33/02 296/184.1 |
| 8,298,594 B1 * | 10/2012 | Turner | | A01M 29/12 424/10.31 |
| 8,647,684 B2 | 2/2014 | Baube | | |
| 8,678,331 B1 * | 3/2014 | Butler | | E04F 15/02183 248/201 |
| 8,889,731 B2 | 11/2014 | Gries et al. | | |
| 8,945,597 B2 | 2/2015 | Zhong | | |
| 2003/0108582 A1 * | 6/2003 | Willis | | A01N 65/00 424/405 |
| 2003/0176545 A1 * | 9/2003 | Behling | | C08K 5/11 524/310 |
| 2003/0213401 A1 * | 11/2003 | Cobham | | A01N 25/02 106/18 |
| 2005/0053797 A1 * | 3/2005 | Rumph | | B05D 7/06 428/541 |
| 2005/0081428 A1 * | 4/2005 | Ramsey | | A01M 7/0046 43/132.1 |
| 2005/0112393 A1 * | 5/2005 | Fliermans | | B27K 3/002 428/537.1 |
| 2005/0153076 A1 * | 7/2005 | Reed | | B05B 15/1225 427/345 |
| 2005/0175656 A1 * | 8/2005 | Toreki | | A01N 33/12 424/410 |
| 2006/0135664 A1 * | 6/2006 | Glassel | | C09G 1/18 524/270 |
| 2009/0056636 A1 * | 3/2009 | Deese | | A01K 5/0142 119/61.53 |
| 2010/0040705 A1 | 2/2010 | Komai et al. | | |
| 2010/0109495 A1 * | 5/2010 | Nelson | | A47B 51/00 144/353 |
| 2011/0229589 A1 * | 9/2011 | Elraz | | A01N 65/00 424/742 |
| 2012/0156517 A1 * | 6/2012 | Vuori | | A01N 37/12 428/541 |
| 2012/0225311 A1 * | 9/2012 | Coleman | | A01N 59/14 428/541 |
| 2013/0259846 A1 | 10/2013 | Dobson | | |
| 2013/0344303 A1 * | 12/2013 | Randall | | A47B 85/06 42/201 |
| 2014/0328884 A1 | 11/2014 | Reyes et al. | | |
| 2014/0329675 A1 * | 11/2014 | Woods | | A01N 43/54 504/100 |
| 2014/0373461 A1 * | 12/2014 | Rodriguez | | E04H 12/2292 52/170 |
| 2015/0004153 A1 | 1/2015 | Jones | | |
| 2015/0208638 A1 * | 7/2015 | Munsell | | A01N 29/12 424/727 |
| 2015/0208657 A1 * | 7/2015 | Ballinger, Jr. | | C08K 5/08 514/732 |
| 2015/0216182 A1 | 8/2015 | Brown et al. | | |
| 2015/0223470 A1 * | 8/2015 | Rodriguez Quintero | | A01N 63/02 504/117 |
| 2015/0264921 A1 * | 9/2015 | Markus | | A01N 65/00 424/408 |
| 2015/0272133 A1 * | 10/2015 | Freeman | | A01N 65/44 424/40 |
| 2016/0242550 A1 * | 8/2016 | Hammock | | A47C 4/30 |
| 2016/0295858 A1 * | 10/2016 | Mason | | A01N 55/00 |

* cited by examiner

NATURAL PESTICIDE STRUCTURES AND METHODS OF FABRICATION THEREOF

CROSS-REFERENCE TO RELATED APPLICATIONS

This application claims the benefit of U.S. provisional application No. 62/286,514, filed Jan. 25, 2016 and entitled NATURAL PESTICIDES AND NATURAL PESTICIDE FABRICATION AND APPLICATION METHODS, and is related to U.S. non-provisional application Ser. No. 15/401,254, filed Jan. 9, 2017 and entitled NATURAL PESTICIDES AND NATURAL PESTICIDE FABRICATION AND APPLICATION METHODS, each of which provisional application and non-provisional application is hereby incorporated by reference herein in its entirety.

FIELD

Illustrative embodiments of the disclosure generally relate to pesticides and pesticide methods. More particularly, illustrative embodiments of the disclosure relate natural pesticide structures and methods of fabricating natural pesticide structures.

BACKGROUND

The background description provided herein is solely for the purpose of generally presenting the context of the illustrative embodiments of the disclosure. Aspects of the background description are neither expressly nor impliedly admitted as prior art against the claimed subject matter.

Insecticides are substances used in agriculture, medicine and industry and by consumers to kill insects. Insecticides played a role in increasing agricultural productivity in the 20th century.

The use of conventional insecticides and other pesticides may have several drawbacks. For example, many pesticides are toxic to humans, pets and other animals. Inorganic compounds of arsenic, such as lead arsenate, have long been used against insect pests. These materials, however, are highly toxic to non-target organisms and may remain in the environment long after their application.

In the United States, the Environmental Protection Agency (EPA) is responsible for regulating pesticides to ensure that these products do not pose adverse effects to humans or the environment. Prior to approval, studies may be conducted to establish the conditions under which the proposed pesticide is safe to use and its effectiveness against the intended pest(s). Some natural pesticides such as organic pesticides may be exempt from regulation.

SUMMARY

Illustrative embodiments of the disclosure are generally directed to methods of fabricating a natural pesticide structure. An illustrative embodiment of the methods includes obtaining at least one raw material; forming at least one natural pesticide building material from the at least one raw material by applying at least one natural pesticide substance to the at least one raw material, the at least one natural pesticide substance having intrinsic pesticide properties and including any combination of the following: garlic, lavender, gardenia, peppermint, wintergreen and lemon grass; and fabricating a natural pesticide structure from the at least one natural pesticide building material.

Another illustrative embodiment of the methods includes obtaining at least one raw material; forming at least one treated pesticide raw material from the at least one raw material by applying at least one natural pesticide substance to the at least one raw material, the at least one natural pesticide substance having intrinsic pesticide properties and including any combination of the following: garlic, lavender, gardenia, peppermint, wintergreen and lemon grass; producing at least one natural pesticide building material from the at least one treated pesticide raw material; and fabricating a natural pesticide structure from the at least one natural pesticide building material.

Illustrative embodiments of the disclosure are generally directed to a natural pesticide structure. An illustrative embodiment of the natural pesticide structure includes a base structure fabricated from at least one natural pesticide building material, the at least one natural pesticide building material fabricated by applying at least one natural pesticide substance to at least one raw material, the at least one natural pesticide substance having intrinsic pesticide properties and including any combination of the following: garlic, lavender, gardenia, peppermint, wintergreen and lemon grass.

BRIEF DESCRIPTION OF THE DRAWINGS

Illustrative embodiments of the disclosure will now be described, by way of example, with reference to the accompanying drawings, in which.

DETAILED DESCRIPTION

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper", "lower", "left", "rear", "right", "front", "vertical", "horizontal", and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise. As used herein, "natural" means "fabricated from substances or raw materials which exist in or are caused by nature and not made or caused by humankind".

Figure 1:
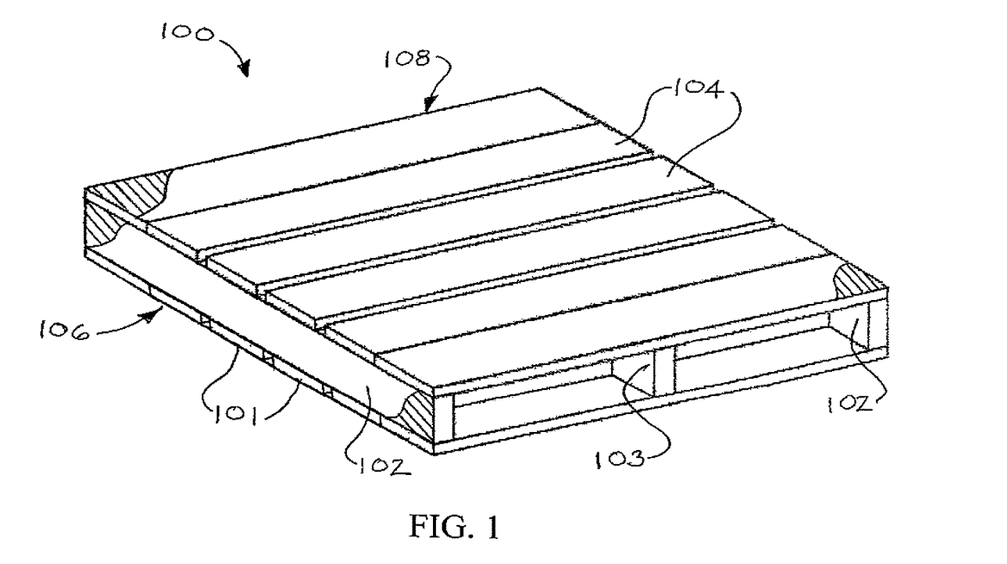
FIG. 1 is a perspective view of a natural pesticide structure in the form of a pallet according to an illustrative embodiment of the disclosure.

Referring initially to FIG. 1 of the drawings, an illustrative embodiment of a natural pesticide structure is generally indicated by reference numeral 100. The natural pesticide structure 100 may include a base structure 108 which is in the form of a pallet and may be fabricated of at least one natural pesticide building material 106. In some non-limiting embodiments, the base structure 108 of the natural pesticide structure 100 may have a pallet design which includes multiple, adjacent, parallel bottom deck boards 101; a pair of parallel, spaced-apart end stringers 102 at the respective ends of the bottom deck boards 101; a center stringer 103 on the bottom deck boards 101 and parallel to and between the end stringers 102; and multiple, adjacent, parallel top deck boards 104 on the end stringers 102 and the center stringer 103. In other non-limiting embodiments, the base structure 108 of the natural pesticide structure 100 may have alternative pallet designs known by those skilled in the art.

Figure 8A:
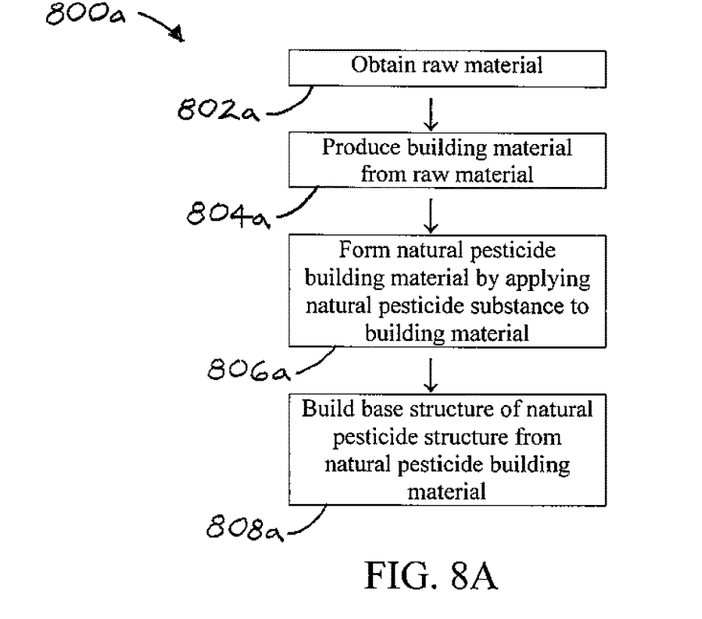
FIG. 8A is a flow diagram of a typical method of fabricating natural pesticide structures according to an illustrative embodiment of the disclosure.

Referring next to FIG. 8A of the drawings, a flow diagram which illustrates a typical method of fabricating the natural pesticide structure 100 in FIG. 1 is generally indicated by reference numeral 800a. At Step 802a, at least one raw material may be obtained. The raw material may include any type of wood or other natural solid material, or any combination of wood and other natural solid material. In some embodiments, the raw material may include at least one natural pesticide raw material having intrinsic pesticide properties. In some non-limiting embodiments, the natural pesticide raw material may include cedar wood. A non-limiting example of cedar wood which is suitable for the natural pesticide raw material includes *Cedrela odorata*, which is a fragrant, insect-repellent and lightweight cedar wood. The raw material may be cut from cedar trees and formed into logs. In some non-limiting embodiments, the raw material may include pine wood and/or cypress wood or any combination of cedar wood, pine wood and cypress wood.

At Step 804a, a building material may be produced from the at least one raw material. This may be accomplished, for example and without limitation, by cutting and processing the raw material using conventional wood cutting, harvesting and processing techniques known by those skilled in the art. In some non-limiting embodiments, the building material may be fabricated by combining two or more raw materials according to the knowledge of those skilled in the art.

At Step 806a, the natural pesticide building material may be formed by applying at least one natural pesticide substance having intrinsic pesticide properties to the building material produced at Step 804a. In some non-limiting embodiments, the natural pesticide substance may include garlic, lavender, gardenia, peppermint, wintergreen, lemon grass, or any combination thereof. In some non-limiting embodiments, the natural pesticide substance may be provided in the form of chips, particles and/or powder, for example and without limitation. The natural pesticide substance may remain physically separate from the building material after application thereto, or alternatively, may be pressed into or otherwise applied or adhered to the building material as a solid according to techniques which are described herein and/or otherwise according to the knowledge of those skilled in the art. In some non-limiting embodiments, the natural pesticide substance may be applied to the building material as an oil or aqueous extract. Liquid forms of the natural pesticide substance may be infused into or applied to the building material by spraying, dipping and/or soaking, for example and without limitation. As a non-limiting example, in some embodiments, garlic in the natural pesticide substance may be obtained as a liquid from Garlic Research Labs, Inc. of Glendale, Calif. Generally, the ratio of the natural pesticide substance to the building material may be about 5%~80% natural pesticide substance to about 95%~20% building material by weight. At Step 808a, the base structure 108 of the natural pesticide structure 100 (FIG. 1) may be fabricated from the natural pesticide building material formed at Step 806a.

Figure 8B:
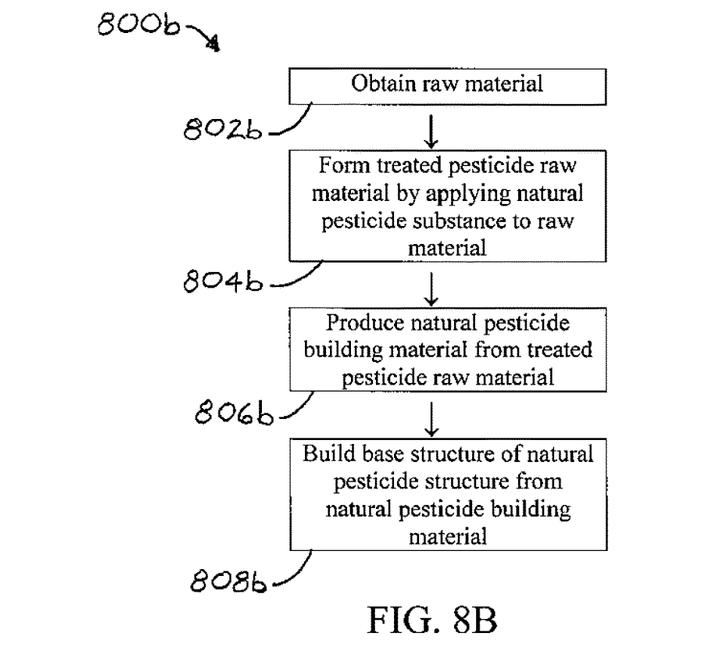
FIG. 8B is a flow diagram of a typical method of fabricating natural pesticide structures according to an alternative illustrative embodiment of the disclosure.

Referring next to FIG. 8B of the drawings, a flow diagram which illustrates a typical alternative method of fabricating the natural pesticide structure 100 in FIG. 1 is generally indicated by reference numeral 800b. At Step 802b, at least one raw material may be obtained. The raw material may include any type of wood or other natural solid material, or any combination of wood and other natural solid material. In some embodiments, the raw material may include at least one natural pesticide raw material having intrinsic pesticide properties. In some non-limiting embodiments, the natural pesticide raw material may include cedar wood. A non-limiting example of cedar wood which is suitable for the natural pesticide raw material includes *Cedrela odorata*, which is a fragrant, insect-repellent and lightweight cedar wood. The raw material may be cut from cedar trees and formed into logs. In some non-limiting embodiments, the raw material may include pine wood and/or cypress wood or any combination of cedar wood, pine wood and cypress wood.

At Step 804b, a treated pesticide raw material may be formed by applying at least one natural pesticide substance having intrinsic pesticide properties to the raw material obtained at Step 802b. In some non-limiting embodiments, the natural pesticide substance may include garlic, lavender, gardenia, peppermint, wintergreen, lemon grass, or any combination thereof. In some non-limiting embodiments, the natural pesticide substance may be provided in the form of chips, particles and/or powder, for example and without limitation. The natural pesticide substance may remain physical separate from the raw material after application thereto, or alternatively, may be pressed or otherwise applied or adhered to or infused into the raw material as a solid according to techniques which are described herein and/or otherwise according to the knowledge of those skilled in the art. In some non-limiting embodiments, the natural pesticide substance may be applied to the raw material as an oil or aqueous extract. Liquid forms of the natural pesticide substance may be applied to or infused into the raw material by spraying, dipping and/or soaking, for example and without limitation. As a non-limiting example, in some embodiments, garlic in the natural pesticide substance may be obtained as a liquid from Garlic Research Labs, Inc. of Glendale, Calif. Generally, the ratio of the natural pesticide substance to the raw material may be about 5%~80% natural pesticide substance to about 95%~20% raw material by weight.

At Step 806*b*, the natural pesticide building material 106 may be produced from the treated pesticide raw material formed at Step 804*b*. This may be accomplished, for example and without limitation, by cutting and processing the treated pesticide raw material using conventional wood cutting, harvesting and processing techniques known by those skilled in the art. In some non-limiting embodiments, the natural pesticide building material may be produced by combining two or more treated pesticide raw materials or by combining one or more treated pesticide materials with one or more natural pesticide raw materials having intrinsic pesticide properties according to the knowledge of those skilled in the art. At Step 808*b*, the base structure 108 of the natural pesticide structure 100 (FIG. 1) may be fabricated from the natural pesticide building material produced at Step 806*b*.

Figure 2:
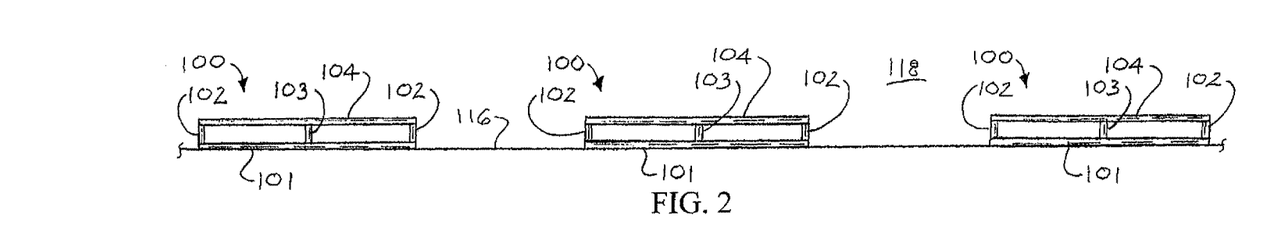
FIG. 2 is a side view of multiple natural pesticide structures in the form of a pallet supported on a floor of a warehouse in typical application of the natural pesticide structure.
Figure 3:
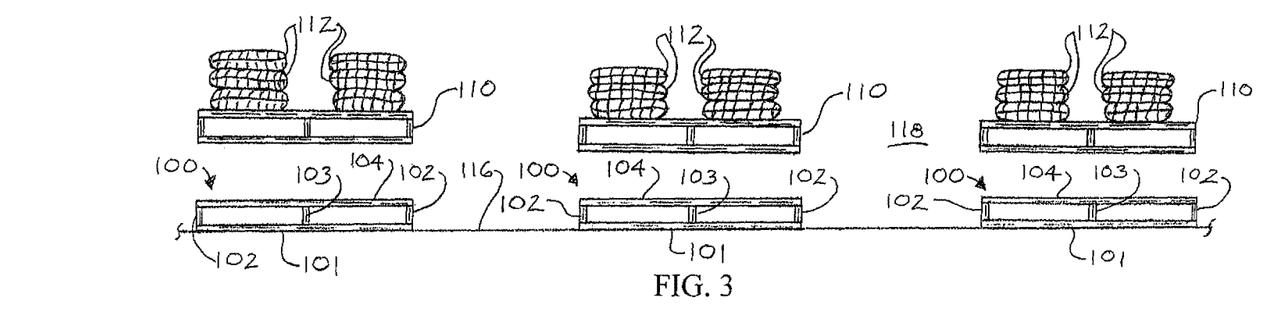
FIG. 3 is a side view of the natural pesticide structures illustrated in FIG. 1, more particularly illustrating placement of multiple transport pallets which support animal feed containers on the respective natural pesticide structures in typical application of the natural pesticide structures.
Figure 4:
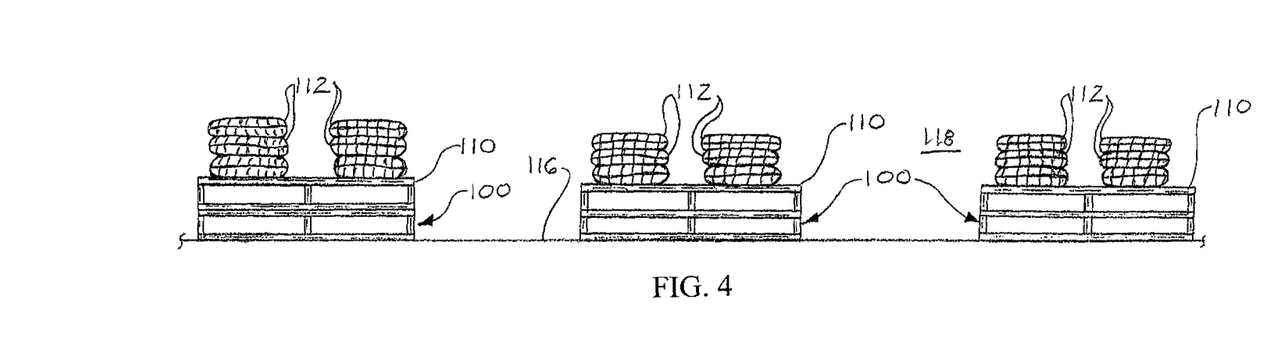
FIG. 4 is a side view of the natural pesticide structures and the transport pallets with animal feed containers on the respective natural pesticide structures.

Referring next to FIGS. 2-4 in conjunction with the flow diagram 900 in FIG. 9, a typical method of using the natural pesticide structure 100 (FIG. 1) having the base structure 108 in the form of a pallet, hereinafter natural pesticide pallet 100, is illustrated. Accordingly, in some non-limiting applications, multiple natural pesticide pallets 100 may be used to support transport pallets 110 on which animal feed containers 112 are carried and stored typically en route to a retail facility or other destination. The animal feed containers 112 may contain a supply of animal feed (not illustrated).

Figure 9:
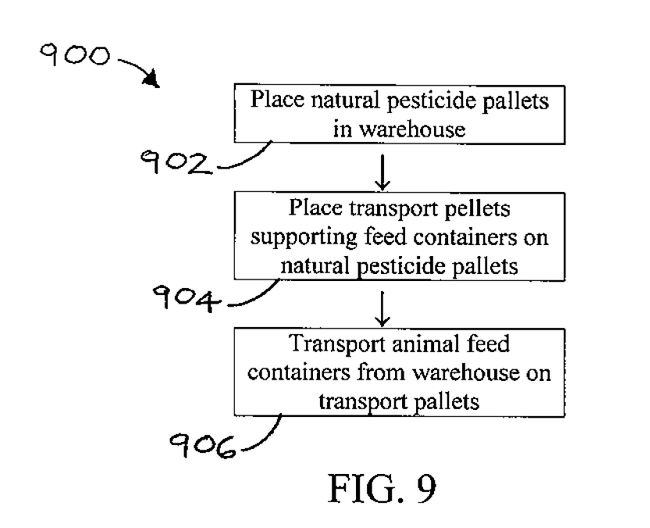
FIG. 9 is a flow diagram of a typical method of using natural pesticide structures in the form of a pallet to support transport pallets which support animal feed containers.

At Step 902 of the flow diagram 900 in FIG. 9, multiple natural pesticide pallets 100 may initially be placed and arranged in desired positions on a floor or other support surface 116 in a feed container warehouse 118, as illustrated in FIG. 2. The transport pallets 110 and animal feed containers 112 thereon may initially be removed from a transport vehicle (not illustrated) using a fork lift or the like (not illustrated). At Step 904 in FIG. 9, the transport pallets 110 may next be placed on the respective natural pesticide pallets 100, as illustrated in FIGS. 3 and 4. Accordingly, as the transport pallets 110 typically remain in place on the respective natural pesticide pallets 100, the natural pesticide pallets 100 may repel and prevent mice, rats, snakes, weevils, ants, roaches and other pests from approaching and scavenging the animal feed in the animal feed containers 112 for as long as the animal feed containers 112 remain in the warehouse 118. Additionally, the natural pesticide building material 106 may repel and prevent termites from feeding on the natural pesticide pallets 100.

At Step 906, the animal feed containers 112 may eventually be transported from the warehouse 118. This may be accomplished typically by lifting the transport pallets 110 from the respective natural pesticide pallets 100. The transport pallets 110 with the feed containers 112 thereon may be placed onto a transport vehicle (not illustrated) which transports the transport pallets 110 and animal feed containers 112 to the destination. The natural pesticide pallets 100 may remain in place on the floor 116 of the feed container warehouse 118 as additional transport pallets 110 on which animal feed containers 112 are supported are subsequently placed on the natural pesticide pallets 100 to repel pests from the animal feed containers 112 in like manner.

Figure 5:
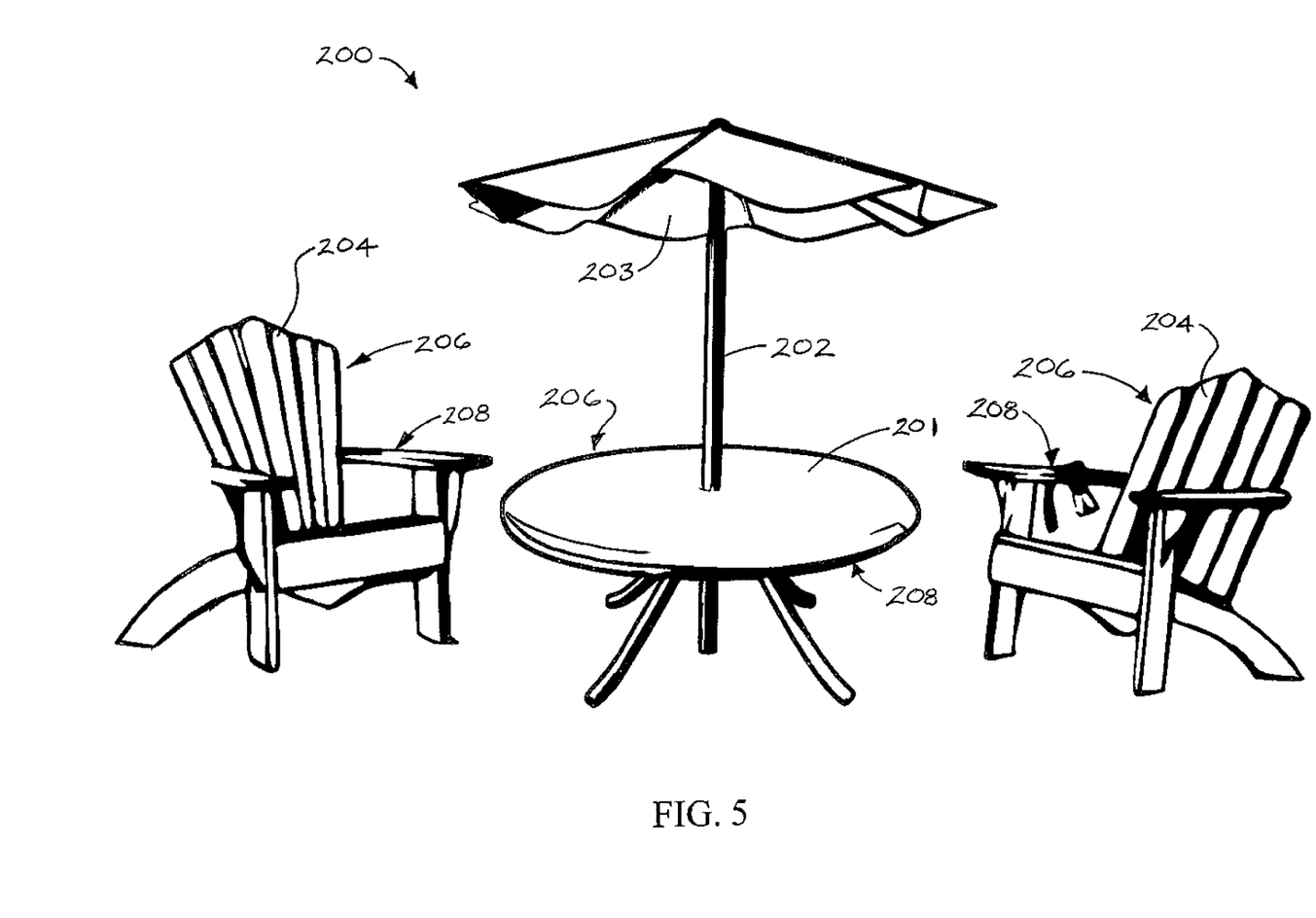
FIG. 5 is a perspective view of a table and a pair of chairs of natural pesticide structures in the form of furniture according to an illustrative embodiment of the disclosure.

Referring next to FIG. 5 of the drawings, an alternative illustrative embodiment of the natural pesticide structure 200 is illustrated. The natural pesticide structure 200 may include a base structure 208 which is in the form of furniture and may be fabricated of at least one natural pesticide building material 206. In some non-limiting embodiments, the base structure 208 of the natural pesticide structure 200 may include a furniture design which includes indoor and/or outdoor furniture, hereinafter natural pesticide furniture 200. For example and without limitation, in some embodiments, the natural pesticide furniture 200 may include a natural pesticide table 201 and/or natural pesticide chairs 204. The natural pesticide table 201 may include a central, upward-standing natural pesticide canopy support 202 with a canopy 203. In other embodiments, the natural pesticide furniture 200 may include a natural pesticide recliner, a natural pesticide beach chair, a natural pesticide cabinet, and/or any other type of furniture which is to be rendered pest-resistant. The natural pesticide furniture 200 may be fabricated of at least one natural pesticide building material 206. Accordingly, the natural pesticide building material 206 of which the natural pesticide furniture 200 is fabricated may repel and prevent mice, rats, snakes, weevils, ants, roaches and other pests from approaching the natural pesticide furniture 200, particularly in the case of outdoor furniture. Additionally, the natural pesticide building material 206 may repel and prevent termites from feeding on the natural pesticide furniture 200. The natural pesticide furniture 200 may be fabricated in the manner which was heretofore described with respect to the flow diagram 800*a* in FIG. 8A or with respect to the flow diagram 800*b* in FIG. 83.

Figure 6:
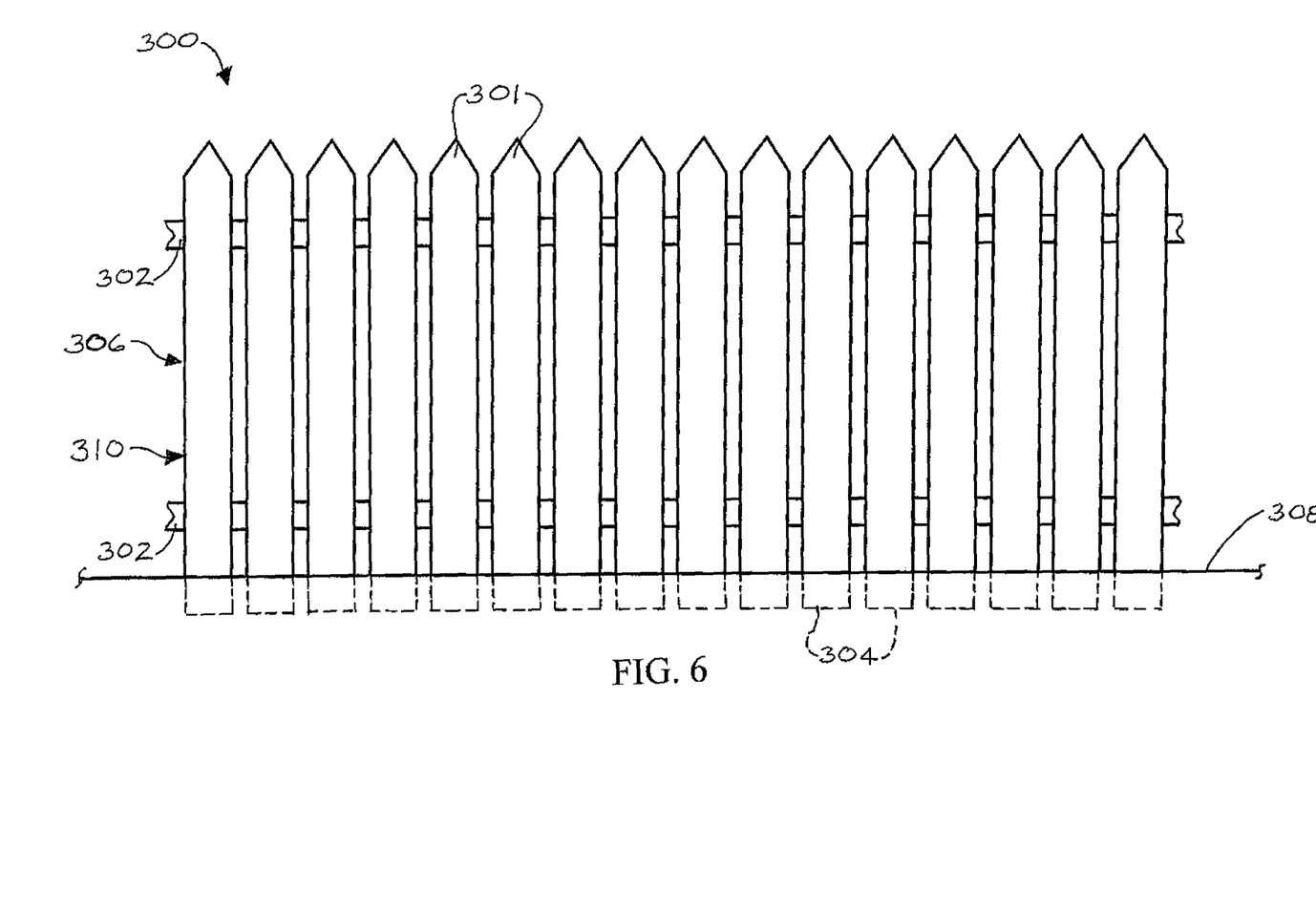
FIG. 6 is a front view of a portion of a natural pesticide structure in the form of a fence according to an illustrative embodiment of the disclosure.

Referring next to FIG. 6 of the drawings, another illustrative embodiment of a natural pesticide structure 300 is illustrated. The natural pesticide structure 300 may include a base structure 310 which is in the form of a fence and may be fabricated of at least one natural pesticide building material 306. In some non-limiting embodiments, the base structure 310 of the natural pesticide structure 300, hereinafter natural pesticide fence 300, may include multiple vertical, adjacent fence boards 301 having lower ends 304. At least one horizontal fence board connecting structure 302 may connect the fence boards 301 in the natural pesticide fence 300. The base structure 310 of the natural pesticide fence 300 may be fabricated in the manner which was heretofore described with respect to the flow diagram 800*a* in FIG. 8A or with respect to the flow diagram 800*b* in FIG. 8B.

In typical application, the natural pesticide fence 300 may be erected to enclose or partition a residential yard or other area (not illustrated). In some embodiments, the lower ends 304 of the fence boards 301 may extend beneath the surface of the ground 308. Accordingly, the natural pesticide building material 306 of which the fence boards 301 and fence board connecting members 302 are fabricated may repel and prevent mice, rats, snakes, weevils, ants, roaches and other pests from approaching and breaching the boundary defined by the natural pesticide fence 300 and entering the enclosed yard or other area (not illustrated). Additionally, the natural pesticide building material 306 may repel and prevent termites from feeding on the fence boards 301 and fence board connecting members 302.

Figure 7:
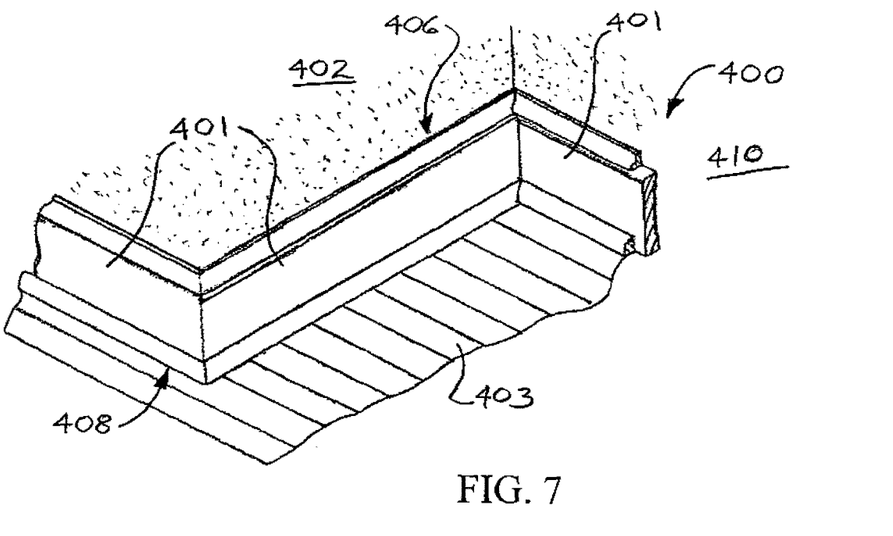
FIG. 7 is a perspective view of a portion of a natural pesticide structure in the form of a baseboard according to an illustrative embodiment of the disclosure.

Referring next to FIG. 7 of the drawings, another illustrative embodiment of a natural pesticide structure 400 is illustrated. The natural pesticide structure 400 may include a base structure 408 which is in the form of a baseboard 401 and may be fabricated of at least one natural pesticide building material 406. In some non-limiting embodiments, the baseboard 401 of the natural pesticide structure 400, hereinafter natural pesticide baseboard 400, may be installed at the junction between a wall 402 and a floor 403 in a room 410 of a home, office building, hotel or other structure. It will be recognized and understood that the natural pesticide structure 400 may include other structures in the room 410, including but not limited to the wall 402, the floor 403, the ceiling (not illustrated) and/or strips of molding (not illustrated) which may be installed between the wall 402 and the ceiling.

The base structure 408 of the natural pesticide baseboard 400 may be fabricated in the manner which was heretofore described with respect to the flow diagram 800*a* in FIG. 8A or with respect to the flow diagram 800*b* in FIG. 8B. Accordingly, the natural pesticide building material 406 of which the baseboard 401 is fabricated may repel and prevent mice, rats, snakes, weevils, ants, roaches and other pests from the room in which the natural pesticide baseboard 400 is installed. Additionally, the natural pesticide building material 406 may repel and prevent termites from feeding on the natural pesticide baseboard 400.

While certain illustrative embodiments of the disclosure have been described above, it will be recognized and understood that various modifications can be made to the embodiments and the appended claims are intended to cover all such modifications which may fall within the spirit and scope of the disclosure.

What is claimed is:

1. A method of fabricating an all-natural pesticide structure, comprising:
   obtaining at least one raw material;
   forming at least one natural pesticide building material from the at least one raw material by applying at least one natural pesticide substance directly to the at least one raw material, the at least one natural pesticide substance having intrinsic pesticide properties and including any combination of the following: garlic, lavender, gardenia, peppermint, menthol and lemon grass; and
   fabricating a natural pesticide structure from the at least one natural pesticide building material.

2. The method of claim 1 wherein obtaining at least one raw material comprises obtaining at least one natural pesticide raw material having intrinsic pesticide properties.

3. The method of claim 2 wherein obtaining at least one natural pesticide raw material having intrinsic pesticide properties comprises obtaining at least one of cedar wood, pine wood, cypress wood and any combination thereof.

4. The method of claim 2 wherein a ratio of the natural pesticide substance to the natural pesticide raw material in the natural pesticide building material is about 5%~40% natural pesticide substance to about 95%~20% natural pesticide raw material by weight.

5. The method of claim 1 wherein fabricating a natural pesticide structure from the at least one natural pesticide building material comprises fabricating a natural pesticide pallet from the at least one natural pesticide building material.

6. The method of claim 1 wherein fabricating a natural pesticide structure from the at least one natural pesticide building material comprises fabricating natural pesticide furniture from the at least one natural pesticide building material.

7. The method of claim 1 wherein fabricating a natural pesticide structure from the at least one natural pesticide building material comprises fabricating a natural pesticide fence from the at least one natural pesticide building material.

8. The method of claim 1 wherein fabricating a natural pesticide structure from the at least one natural pesticide building material comprises fabricating a natural pesticide baseboard from the at least one natural pesticide building material.

9. A method of fabricating an all-natural pesticide structure, comprising:
   obtaining at least one natural pesticide raw material having intrinsic pesticide properties;
   forming at least one treated pesticide raw material from the at least one raw material by applying at least one natural pesticide substance directly to the at least one raw material, the at least one natural pesticide substance having intrinsic pesticide properties and including any combination of the following: garlic, lavender, gardenia, peppermint, menthol and lemon grass;
   producing at least one natural pesticide building material from the at least one treated pesticide raw material; and
   fabricating a natural pesticide structure from the at least one natural pesticide building material.

10. The method of claim 9 wherein obtaining at least one natural pesticide raw material having intrinsic pesticide properties comprises obtaining at least one of cedar wood, pine wood, cypress wood and any combination thereof.

11. The method of claim 9 wherein a ratio of the natural pesticide substance to the natural pesticide raw material in the natural pesticide building material is about 5%~80% natural pesticide substance to about 95%~20% natural pesticide raw material by weight.

12. The method of claim 9 wherein fabricating a natural pesticide structure from the at least one natural pesticide building material comprises fabricating a natural pesticide pallet from the at least one natural pesticide building material.

13. The method of claim 9 wherein fabricating a natural pesticide structure from the at least one natural pesticide building material comprises fabricating natural pesticide furniture from the at least one natural pesticide building material.

14. The method of claim 9 wherein fabricating a natural pesticide structure from the at least one natural pesticide building material comprises fabricating a natural pesticide fence from the at least one natural pesticide building material.

15. The method of claim 9 wherein fabricating a natural pesticide structure from the at least one natural pesticide building material comprises fabricating a natural pesticide baseboard from the at least one natural pesticide building material.

16. An all-natural pesticide structure, comprising:
   a base structure fabricated from at least one natural pesticide building material, the at least one natural pesticide building material fabricated by applying at least one natural pesticide substance directly to at least one raw material, the at least one natural pesticide substance having intrinsic pesticide properties and including any combination of the following: garlic, lavender, gardenia, peppermint, menthol and lemon grass.

17. The natural pesticide structure of claim 16 wherein the base structure is a pallet, furniture, a fence or a baseboard.

18. The natural pesticide structure of claim 16 wherein the at least one raw material comprises at least one natural pesticide raw material having intrinsic pesticide properties, the at least one natural pesticide raw material including at least one of cedar wood, pine wood, cypress wood and any combination thereof.

19. The natural pesticide structure of claim 18 wherein a ratio of the natural pesticide substance to the natural pesticide raw material in the natural pesticide building material is about 5%~80% natural pesticide substance to about 95%~20% natural pesticide raw material by weight.

* * * * *